(12) United States Patent
Brenchley

(10) Patent No.: US 9,764,078 B2
(45) Date of Patent: Sep. 19, 2017

(54) EXTRACORPOREAL REMOVAL OF ANTI-IQCJ ANTIBODIES FROM BLOOD

(71) Applicant: The University of Manchester, Manchester (GB)

(72) Inventor: Paul E. C. Brenchley, Sale (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 14/732,212

(22) Filed: Jun. 5, 2015

(65) Prior Publication Data

US 2015/0352274 A1 Dec. 10, 2015

Related U.S. Application Data

(60) Provisional application No. 62/008,895, filed on Jun. 6, 2014.

(51) Int. Cl.
*A61M 1/14* (2006.01)
*A61M 1/36* (2006.01)
*G01N 33/68* (2006.01)

(52) U.S. Cl.
CPC .......... *A61M 1/3687* (2013.01); *A61M 1/362* (2014.02); *G01N 33/6854* (2013.01); *A61M 2202/0413* (2013.01); *G01N 2800/347* (2013.01); *G01N 2800/52* (2013.01)

(58) Field of Classification Search
None
See application file for complete search history.

(56) References Cited

U.S. PATENT DOCUMENTS 8,741,580 B2 * 6/2014 Kienle ................ C12Q 1/6883
435/7.1

OTHER PUBLICATIONS

Pairwise alignment scores (http://www.ncbi.nlm.nih.gov/homologene?cmd=Retrieve&dopt=AlignmentScores&list_uids=132095) , accessed Aug. 23, 2016.*
Kwasnicka-Crawford et al., BBRC 350:890-899, 2006.*
Lennon et al., Feb. 26, 2014, Poster 47 (Published Online).*

* cited by examiner

*Primary Examiner* — Lorraine Spector
(74) *Attorney, Agent, or Firm* — Faegre Baker Daniels LLP

(57) ABSTRACT

Some aspects of the invention include methods of treating a patient who has or is at risk of developing kidney disease, methods of selecting a suitable regimen for the prevention or treatment of kidney disease, and to methods of monitoring the effectiveness of a treatment regimen for the prevention or treatment of kidney disease. Other aspects of the invention include medical uses of a binding partner for an anti-IQCJ antibody, and methods of preventing or treating kidney disease in a subject using such binding partners. Still other aspects of the invention include devices for the extracorporeal treatment of a patient's blood.

7 Claims, 22 Drawing Sheets

EXTRACORPOREAL REMOVAL OF ANTI-IQCJ ANTIBODIES FROM BLOOD

PRIORITY CLAIM

This is a U.S. Non-Provisional Application, which claims the benefit of U.S. Provisional Application No. 62/008,895, filed on Jun. 6, 2014. The entire disclosures of which is hereby expressly incorporated herein by reference.

FIELD OF THE INVENTION

Some aspects of the invention relate to methods of treating a patient who has or is at risk of developing kidney disease, and methods of monitoring the effectiveness of a treatment regimen for the prevention or treatment of kidney disease. Other aspects relate to medical uses of a binding partner for an anti-IQCJ antibody, and methods of preventing or treating kidney disease in a subject using such binding partners. Other aspects also relate to devices for the extracorporeal treatment of a patient's blood.

SUMMARY AND BACKGROUND

The causes of chronic kidney disease (CKD) are many but can be grouped into the three main areas of diabetes, glomerulonephritis (inflammation in the kidney) and a collection of single gene defects (polycystic kidney disease being the most common gene defect). Glomerulonephritis (GN) accounts for 25-30% of CKD and is often diagnosed when patients present with proteinuria and/or haematuria. If proteinuria is greater than 3.5 gm/24 hr, the patient may present with nephrotic syndrome which is associated with oedema, and increased risk of thromboembolism and cardiovascular disease. Classically, GN is diagnosed following renal biopsy and histopathological analysis of the glomerular pathology, where structural changes in the glomerulus revealed by light and electron microscopy in combination with immunostaining allow classification into types of glomerulonephritis. Incidences of GN vary across the world due to two major variables, firstly the frequency and use of renal biopsy and secondly the ethnic genetic background of the country/region. In adults, nephrotic syndrome is most commonly caused by membranous nephropathy (MN, 8-12 cases per million population), and focal segmental glomerulonephritis (FSGS, 2-5 cases per million population) Hanko J 2009, Mcquarrie 2010. In children, cases of nephrotic syndrome are estimated at 160 case per million children, with 80% caused by steroid sensitive nephrotic syndrome (minimal change disease) and 20% by steroid resistant nephrotic syndrome (FSGS) (Gbadegesin 2012). IgA nephropathy, commonly presenting in both adults and children with haematuria with or with proteinuria and hypertension is the commonest biopsy finding with mesangial deposits of IgA and complement C3.

While biopsy classification coupled with clinical presentation provides a framework for understanding each type of renal disease, there is often wide variation between patients in disease activity, severity, response to immunosuppression and clinical outcome. Biopsy may not truly reflect the disease process due to sampling errors and is just a snapshot that can't be repeated as a routine management tool on a frequent basis.

What is required is one or more biomarkers of each specific disease mechanism that act as true surrogates of the mechanism such that by monitoring these markers, clinical management information on the disease activity, severity, response to treatment and outcome is obtained. A recent example of what appears to be a good surrogate marker of the disease mechanism in idiopathic membranous nephropathy is the autoantibody anti-PLA2R (Beck et al 2009)

IQCJ was identified as a partner in a novel human fusion gene IQCJ-SCHIP1 in 2006 in the context of genetic investigations in an individual with a 3q25-q29 inversion and language delay. Exploration of IQCJ-SCHIP1 expression in studies on human tissue identified two transcripts predominantly in fetal and adult brain and incidentally in kidney. In cultured neuronal cells IQCJ-SCHIP1 interacts with calmodulin through the conserved IQ domain and has been shown to align to actin filaments in neurite extensions.

Some aspects of the invention include methods of treating a patient who has or is at risk of developing kidney disease.

Other aspects include medical uses of a binding partner for an anti-IQCJ antibody, and methods of preventing or treating kidney disease in a subject using such binding partners.

Still other aspects include devices for the extracorporeal treatment of a patient's blood.

In a first aspect, the invention provides a method of diagnosing kidney disease in a subject, the method comprising: assaying a sample of a body fluid for the presence of an anti-IQCJ antibody in the subject's body fluid, wherein the presence of an anti-IQCJ antibody in the sample indicates that the subject has kidney disease.

In a second aspect, the invention provides a method of selecting a suitable regimen for the prevention or treatment of kidney disease, the method comprising: assaying a sample of a body fluid for the presence of an anti-IQCJ antibody in the subject's body fluid, wherein the presence of an anti-IQCJ antibody in the sample indicates that the subject will benefit from a regimen for prevention or treatment of kidney disease utilising a binding partner for an anti-IQCJ antibody.

In a third aspect, the invention provides a method of monitoring effectiveness in a subject of a treatment regimen for prevention or treatment of kidney disease, the method comprising: assaying a sample of a body fluid of a subject undergoing a treatment regimen for prevention or treatment of kidney disease, to obtain a value representative of the amount of anti-IQCJ antibodies present in the subject's body fluid sample; comparing the value obtained with a reference value; and based on this comparison, determining whether the subject's treatment regimen is effective for prevention or treatment of kidney disease.

Methods of the first or second aspects of the invention may further comprise obtaining a value representative of the amount of anti-IQCJ antibodies present in the sample from the subject, and comparing this obtained value with a reference value. Examples of such embodiments are discussed further below.

As discussed further below, methods in accordance with the first, second, or third aspects of the invention may optionally further comprise a step of implementing a suitable regimen for the prevention or treatment of kidney disease. More details of these embodiments are provided elsewhere in the specification.

Alternatively or additionally, the methods of the first, second, or third aspects of invention may further comprise assessment of one or more additional markers indicative of kidney disease. Examples of such additional markers are considered elsewhere in the specification.

In a fourth aspect, the invention provides a binding partner for an anti-IQCJ antibody for use in the prevention or treatment of kidney disease.

In a fifth aspect, the invention provides a method of preventing or treating kidney disease in a subject, the method comprising: contacting a volume of the subject's blood with a binding partner for an anti-IQCJ antibody, such that anti-IQCJ antibodies present in the subject's blood are able to bind to and be retained by the binding partner; and separating the binding partner and bound anti-IQCJ antibody from the blood, to yield an antibody-depleted volume of blood.

In a sixth aspect, the invention provides a device for extracorporeal treatment of a patient's blood, the device comprising: a binding partner for an anti-IQCJ antibody; and means for separating the binding partner from blood.

A first embodiment of the invention includes a method of treating a patient, said method comprising the steps of: contacting a binding partner for an anti-IQCJ antibody with a portion of a body fluid, wherein the fluid is from a patient; and determining the presence of an anti-IQCJ antibody in the subject's body fluid using a technique selected from the group consisting of: enzyme linked immunosorbent assays (ELISAs), western blotting, fluorescent bead-based immunoassays, and immunofluorescence on cell expressed IQCJ.

A second embodiment of the invention includes the method according to the first embodiment, further comprising the step of: treating the patient for kidney disease.

A third embodiment of the invention includes the method according to the first embodiment, further comprising the steps of: obtaining a value representative of the amount of anti-IQCJ antibodies in the patient's bodily fluid; and comparing the obtained value with a reference value.

A fourth embodiment of the invention includes the method according to the first embodiment, further comprising the step of: determining the presence of at least one marker selected from the group consisting of: anti-PLA2R antibodies; anti-nephrin antibodies; and anti-podocin antibodies in the patient's bodily fluid.

A fifth embodiment of the invention includes the method according to the second embodiment, wherein the patient is treated for at least one kidney disease selected from the group consisting of: primary renal failure, membranous nephropathy, de novo membranous nephropathy, IQCJ podocytopathy, and focal segmental glomerulosclerosis.

A sixth embodiment of the invention includes the method according to the first embodiment, wherein the bodily fluid is selected from the group consisting of: blood, serum, plasma, urine, and interstitial fluid.

A seventh embodiment of the invention includes the method according to the first embodiment, wherein said binding partner comprises an epitope recoginzed by the anti-IQCJ antibodies.

An eighth embodiment of the invention includes the method according to the seventh embodiment, wherein said binding partner includes at least one compound selected from the group consisting of: a compound that has 70% identity with SEQ ID NO:1 and a compound that has 100% identity with SEQ ID NO:1.

A ninth embodiment of the invention includes the method according to the seventh embodiment, wherein said binding partner further comprises a retention moiety selected from the group consisting of: a magnetic bead and a substrate.

A tenth embodiment of the invention includes a device for extracorporeal treatment of a patient's blood, the device comprising: a binding partner for an anti-IQCJ antibody; and an insoluble structure, wherein said binding partner comprises an epitope recognized by the anti-IQCJ antibodies, and wherein the insoluble structure is attached to the binding partner.

An eleventh embodiment of the invention includes the device according to the tenth embodiment, wherein the insoluble structure includes at least one material is selected from the group consisting of: cellulose, cellulose derivatives, agarose, agarose derivatives, polysulphone, polysulphone derivatives, polyacrylamide, polyacrylamide derivatives, and nylon.

A twelfth embodiment of the invention includes the device according to the eleventh embodiment, wherein the insoluble structure is selected from the group consisting of: hollow fibre cassettes, membranes, and beads.

A thirteenth embodiment of the invention includes a method of preventing or treating kidney disease comprising the steps of: contacting a portion of a patient's blood with an anti-IQCJ antibody; retaining the binding partner that is bound to the anti-IQCJ antibody in the portion of the patient's blood; and separating the binding partner and the bound anti-IQCJ antibody from the blood of the patient.

A fourteenth embodiment of the invention includes the method according to the thirteenth embodiment, wherein said binding partner includes at least one compound selected from the group consisting of: a compound that has 70% identity with SEQ ID NO:1 and a compound that has 100% identity with SEQ ID NO:1.

A fifteenth embodiment of the invention includes the method according to the fourteenth embodiment, wherein said binding partner further comprises a retention moiety selected from the group consisting of: a magnetic bead and a substrate.

A sixteenth embodiment of the invention includes the method according to the thirteenth embodiment, wherein the contacting step, the retaining step, and the separating step are performed extracorporeally.

A seventeenth embodiment of the invention includes the method according to the sixteenth embodiment, further comprising the step of: providing the antibody-depleted blood back to the patient.

An eighteenth embodiment of the invention includes the method according to the sixteenth embodiment, wherein the binding partner is provided in an arrangement so that the patient's blood may flow over the binding partner, thus allowing it to bind anti-IQCJ antibodies in the blood.

A nineteenth embodiment of the invention includes the method according to the thirteenth embodiment, wherein the patient has or is at risk of developing at least one kidney disease selected from the group consisting of: primary renal failure, membranous nephropathy, de novo membranous nephropathy, IQCJ podocytopathy, and focal segmental glomerulosclerosis.

A twentieth embodiment of the invention includes the method according to the thirteenth embodiment, wherein the contacting step, the retaining step, and the separating step are carried out "in line."

BRIEF DESCRIPTION OF THE SEQUENCES

Figure 1A:
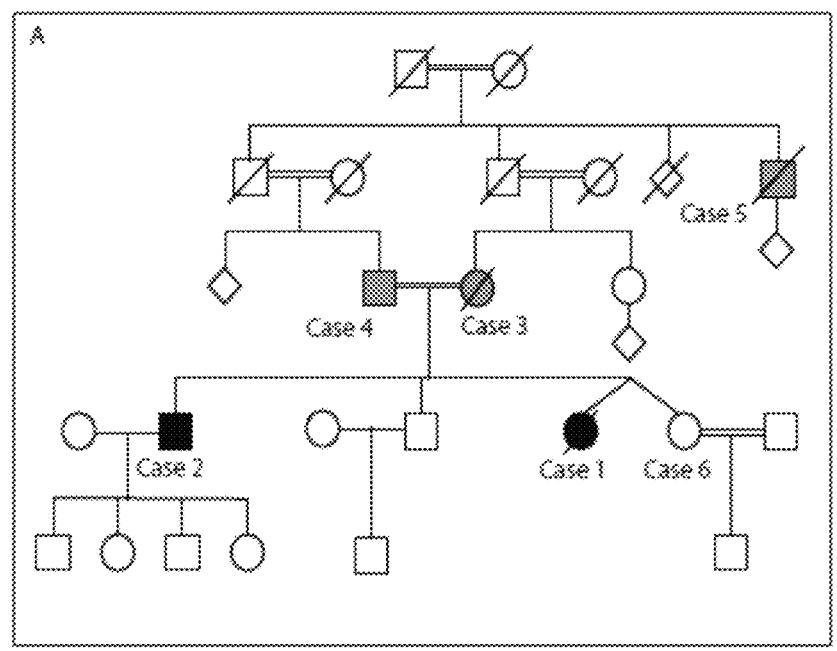
FIG. 1A. Table illustrating family pedigree. Black filled symbols represent siblings affected by primary podocytopathy and post-transplant membranous nephropathy. Gray symbols represent other family members affected by renal disease.

SEQ ID NO:1 is an amino acid sequence of the IQCJ protein

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

The various aspects and embodiments of the present invention disclosed herein are based upon the inventors' finding that the protein IQCJ is associated with kidney function, and that the presence of antibodies that bind to IQCJ is associated with kidney disease. Autoantibodies against IQCJ are indicative of the presence of kidney disease, and contribute to the development and progression of such disease.

In contrast, if antibodies against IQCJ have their activity or concentrations lowered, for example through the actions of binding partners that associate with the anti-IQCJ antibodies allowing their removal, then this reduces the damage occurring, and so allows kidney disease to be prevented or treated.

The various aspects and embodiments of the invention will be described further below to aid in the understanding of the invention. In keeping with this aim, certain terms used in the disclosure are further described or defined in the following paragraphs.

Anti-IQCJ Antibodies

References to anti-IQCJ antibodies in the present disclosure may be taken as encompassing any antibody reactive to the IQCJ protein (the amino acid sequence of the wild type form of which is shown in SEQ ID NO:1).

The skilled person will be aware of many suitable methods by which the ability of an antibody to bind to IQCJ may readily be determined. Merely by way of example, the enzyme linked immunosorbent assays (ELISAs) discussed further elsewhere in the specification (including in the Examples) may be used to assess an antibody's ability to bind to IQCJ.

In a suitable embodiment the anti-IQCJ antibodies may be IgG antibodies. Knowledge of the immunoglobulin type of the anti-IQCJ antibodies is useful when selecting methods for the detection of such antibodies.

Suitably, the anti-IQCJ antibodies may be autoantibodies, which is to say antibodies raised by a subject against their own IQCJ protein. It will also be recognized that the nature of the antibodies in question will be determined by the identity of the subject. For example, a human subject will have human antibodies, and a feline subject will have feline antibodies.

Kidney Disease

Specific examples of "kidney disease" that may be diagnosed, prevented or treated by the methods, uses or medicaments of the invention may be selected from the group consisting of: primary renal failure; membranous nephropathy, such as de novo membranous nephropathy; IQCJ podocytopathy; and focal segmental glomerulosclerosis.

The inventors believe that the present of anti-IQCJ antibodies is able to contribute to the damage and disease progression associated with each of these kidney diseases, Body Fluid Samples Certain aspects of the invention investigate samples of a body fluid from a subject for the presence, or amount, of anti-IQCJ antibodies therein.

In a suitable embodiment, the body fluid is selected from the group consisting of: blood; serum; plasma; urine; saliva, and interstitial fluid.

The sample may be one that is obtained from the subject, for example by taking of a blood, saliva, or interstitial fluid sample, or provision of a urine sample, and this step of obtaining the sample may optionally be part of the method in question.

A Subject

For the purposes of the present invention, a subject may be an individual or a patient identified as having, or potentially as having (for example, as at risk of having) kidney disease. The nature of an appropriate subject will be apparent to a skilled reader depending on the aspect of the invention in question.

Merely by way of example, in the case of a method of diagnosis in accordance with the invention, a suitable subject may be one that is considered to be at risk of kidney disease. This assessment of risk may be based upon predisposing factors, such as genetic predisposition to kidney disease, or on the exhibition of symptoms consistent with kidney disease. Alternatively, a suitable subject for a method of diagnosis in accordance with the invention may be an individual exhibiting clinical symptoms of kidney disease, but where the cause or nature of the kidney disease has not been identified.

In a method of preventing or treating kidney disease in accordance with the invention, a suitable subject may be one diagnosed as having kidney disease (for example by a method of the invention) or as exhibiting symptoms consistent with kidney disease. Indeed, the subject may be an individual where this regimen for prevention or treatment has been selected as being suitable by a method of the invention.

In the case of the invention's methods of selecting a suitable regimen for the prevention or treatment of kidney disease, a suitable subject may be an individual diagnosed as having kidney disease, but where the cause of the kidney disease has not been determined In the event that the method of the invention indicates that anti-IQCJ antibodies are present within the subject, this suggests that these antibodies are contributing to the disease process, and that a regimen utilizing a binding partner for an anti-IQCJ antibody in a therapeutic manner is likely to be suitable for prevention or treatment of the kidney disease.

In the case of a method of monitoring effectiveness in a subject of a treatment regimen for prevention or treatment of kidney disease, a suitable subject may be a patient undergoing therapy for kidney disease (for example by a method of prevention or treatment of the invention, or by pharmaceutical compositions or medical uses of the invention). In this case, the method of the invention may be used as part of a process of ongoing care for the subject, with a view to optimizing a regimen for prevention or treatment of the disease, or ensuring that a selected regimen remains effective. Alternatively, it will be recognized that methods of monitoring effectiveness in a subject are also suitable for use in the development of novel prevention or treatment regimens, such as by clinical trials.

The fifth aspect of the invention relates to methods of preventing or treating kidney disease practiced in respect of subjects requiring such prevention or treatment. A suitable subject requiring such prevention or treatment may be one diagnosed as having kidney disease, or otherwise exhibiting symptoms consistent with the presence of kidney disease.

Diagnosis of Kidney Disease

The first aspect of the invention provides a method of diagnosing kidney disease. In suitable embodiments, methods in accordance with this aspect of the invention may be carried out in vitro.

As referred to above, methods of diagnosing kidney disease in accordance with the present invention may be useful for the clinical assessment of individuals considered at risk of kidney disease, individuals suffering a disorder that may be kidney disease, or subjects who have already been identified as having kidney disease, but without the underlying cause of the kidney disease having been determined In these later cases the diagnostic methods of the invention may be useful in determining that the kidney disease is one associated with the presence of anti-IQCJ antibodies.

A method of diagnosing kidney disease in accordance with the first aspect of the invention may further involve obtaining a value representative of the amount of anti-IQCJ antibodies present in the subject's body fluid sample, and comparing this obtained value with a reference value. It may then be determined whether or not anti-IQCJ antibodies are present in the sample at a greater amount than in the reference value. In such cases, an obtained value greater than the reference value may be indicative that the subject has kidney disease. Details of suitable reference values that may be employed in such embodiments are discussed elsewhere in the present disclosure.

Selection of a Suitable Regimen for the Prevention or Treatment of Kidney Disease The second aspect of the invention comprises a method for the selection of a suitable regimen for the prevention or treatment of kidney disease. The skilled person will appreciate that there are many different forms and causes of kidney disease, as well as many different agents and regimens for the treatment of such disease. Not all treatment regimens are suitable for prevention or alleviation of all forms of kidney disease.

The aspects of the present invention relating to the selection of a suitable treatment or prevention regimen are based upon the inventor's finding that anti-IQCJ antibodies generated by a patient's body against the naturally occurring target protein are responsible for certain forms of kidney disease (examples of which are considered elsewhere in this specification).

By determining whether anti-IQCJ antibodies are present in a subject these methods of the invention make it possible to identify whether or not the subject in question is one who will benefit from treatment aimed at neutralizing or removing these antibodies (and thereby preventing further damage that the antibodies may cause) by use of binding partners to the anti-IQCJ antibodies.

Various optional modifications of methods of the invention, including these methods in accordance with the second aspect of the invention, are considered within the present disclosure.

Monitoring Effectiveness of a Treatment Regimen

The third aspect of the invention provides a method of monitoring effectiveness in a subject of a treatment regimen for prevention or treatment of kidney disease. As set out elsewhere, the methods of the third aspect of the invention involve obtaining a value indicative of the amount of anti-IQCJ antibodies in a sample from a subject, and comparing this with a reference value. Generally, if the obtained value is lower than the reference value this indicates that the treatment regimen is effective. In such cases the lower the obtained value, as compared to the reference value, the more effective the treatment regimen.

Methods of the invention in accordance with this aspect are suitable for use in a number of different contexts in which it is wished to assess whether or not a treatment regimen is able to effectively prevent or treat kidney disease.

Merely by way of example, methods in accordance with this third aspect of the invention are suitable for use in the field of personalized medicine. Here such methods of the invention are able to determine on a patient by patient basis whether or not a proposed treatment regimen proves effective. In the event that a proposed treatment regimen is identified as ineffective it can be modified in an attempt to improve effectiveness, or replaced, and a different regimen tested for efficacy.

These methods of the invention also allow effectiveness of different methods to be determined and compared with one another, wherein the treatment regimen giving rise to the lowest antibody levels will generally be considered the most effective. Thus, even in the event that a given treatment regimen is determined to be effective by the monitoring methods of the present invention, other treatment regimens that are more effective may be identified, and a decision made to adopt a more effective treatment regimen for future prevention or treatment.

As referred to elsewhere, it will also be recognized that methods of monitoring effectiveness of a treatment regimen in accordance with this aspect of the invention are also suitable for use in the development of novel prevention or treatment regimens. Here a putative treatment regimen may be adopted, and its effectiveness in reducing anti-IQCJ antibody levels assessed, with those that bring about a reduction selected for future use, or for further refinement. Such methods may be useful in the context of clinical trials or the like.

Assaying for Anti-IQCJ Antibodies

A number of the methods of the invention (such as methods of the first, second, or third aspects of the invention) involve assaying a sample of a body fluid from a subject for the presence or amount of anti-IQCJ antibodies within the body fluid. The skilled person will be able to determine a number of suitable methods by which such assays for anti-IQCJ antibodies may be practiced. The following provides some examples of such assays, as well as guidance regarding factors that may be considered in determining a suitable assay to be used in practicing the invention.

Generally, assays for anti-IQCJ antibodies suitable for use in the methods of the invention may be qualitative or quantitative in nature.

In methods of the invention that require a determination as to the presence (or otherwise) of anti-IQCJ antibodies in a sample, a suitable assay may be either qualitative or quantitative.

Those aspects of the invention that require a value representative of the amount of anti-IQCJ antibodies present in a body fluid sample to be obtained will require the use of a quantitative assay.

Suitable assays by which the presence of anti-IQCJ antibodies may be detected, and optionally quantitated, include those selected from the group consisting of: enzyme linked immunosorbent assays (ELISAs); western blotting; fluorescent bead-based immunoassays; and immunofluorescence on cell expressed IQCJ.

Merely by way of example, in a suitable embodiment the ELISA may use an immobilized binding partner for an anti-IQCJ antibody (in keeping with the definitions set out elsewhere in the specification, and which may suitably be recombinant IQCJ) to capture anti-IQCJ antibodies in a sample. The captured anti-IQCJ antibodies may then be detected by means of a labelled antibody directed to the immunoglobulin class to which the anti-IQCJ antibodies belong. For example, in the case of anti-IQCJ antibodies comprising IgG, the presence of such antibodies may be determined by use of a labelled (for example peroxidase labelled) anti-human-IgG antibody. Further details of a suitable embodiment of an assay of this sort are set out in the Examples section of this specification.

In a suitable embodiment assaying of the body fluid sample for anti-IQCJ antibodies is conducted in vitro.

Reference Value

The methods of monitoring effectiveness in a subject of a treatment regimen for prevention or treatment of kidney disease disclosed herein involve obtaining a value representative of the amount of anti-IQCJ antibodies present in a body fluid sample from a subject, and comparing this obtained value to a reference value.

Furthermore, certain embodiments of methods of the first or second aspects of the invention optionally involve obtaining a value representative of the amount of anti-IQCJ antibodies present in a body fluid sample, and comparing this value to a reference value.

A number of different values may be used as the reference value in such methods of the invention, and selection of an appropriate reference value will determine the nature of the conclusion that may be drawn using the method of the invention.

In certain embodiments of the invention, a suitable reference value may be one representative of a "background" amount of anti-IQCJ antibodies that may be detectable in a sample without indicating the presence of kidney disease. This baseline may reflect the limit of detection of the assay, or the incidence of false positive results. Reference values of this sort may be suitable for use in the methods of the first or second aspects of the invention.

A suitable reference value reflecting a background level of anti-IQCJ antibodies may be established by assaying approximately 30 sample (for example, 25 or more, 26 or more, 27 or more, 28 or more, 29 or more, or 30 or more samples), from normal healthy individuals without kidney disease, to obtain values representative of the amounts of anti-IQCJ antibodies in these samples. In such an embodiment, the reference value (functioning as a threshold between samples considered positive or negative for kidney disease) may be set at the mean value from the healthy individuals, plus three standard deviations (SDs). In such cases an obtained value above the reference value will be indicative of kidney disease in the subject from whom the value has been obtained, while an obtained value below the reference value will indicate that kidney disease is not present in the subject.

The normal healthy individuals may be matched controls with reference to the subject in respect of whom the method of the invention is to be practiced (for example, the healthy individuals may be matched with respect to gender and/or age), or the healthy individuals may be a panel of individuals (for example, a panel of male and/or female individuals having a range of ages that approximately matches the group in whom kidney disease is to be investigated).

In a suitable embodiment of the methods of the third aspect of the invention, the reference value is representative of the amount of anti-IQCJ antibodies present in a comparable sample from the subject at an earlier time point.

In methods of the third aspect of the invention, comparison of the value obtained from the subject with the reference value will provide valuable information as to the effectiveness or ineffectiveness of a treatment regimen. Generally, if the value obtained in respect of the amount of anti-IQCJ antibodies present in the subject's body fluid is lower than the reference value, then this will indicate that the treatment regimen that the subject is undergoing is effective. If the obtained value is higher than the reference value, indicating that the amount of anti-IQCJ antibodies present in the subject's body fluid is elevated as compared to the reference value, this will indicate that the treatment regimen that the subject is undergoing is ineffective. In such cases the treatment regimen may require revision, and the methods of the invention may then be performed again (once the revision has had time to alter the amount of anti-IQCJ antibodies present in the subject) to assess the effectiveness of the revised regimen.

In another embodiment of the methods of the third aspect of the invention, a first sample is assayed to obtain a first value representative of the amount of anti-IQCJ antibodies present in the subject's body fluid, and a second sample is assayed to obtain a second value representative of the amount of anti-IQCJ antibodies present in the subject's body fluid at a second, later, timepoint, after treatment with a treatment regimen of interest. The first and second obtained values are compared with a reference value indicative of the background level of anti-IQCJ antibodies. If the second obtained value is closer to the reference value than is the first obtained value, then this indicates that the treatment regimen is effective. If the first obtained value is closer to the reference value, or if the two obtained values are the same, this indicates that the treatment regimen is ineffective.

Suitable samples used in the generation of reference values may be of any body fluid, such as sera, as considered elsewhere in the present specification. Samples used for the generation of reference values may by matched, with reference to type, with the sample from which the obtained value is derived. Samples found to contain anti-IQCJ antibodies may be used to create a standard dilution curve as a reference point for comparison with other samples.

Optional Modifications of Methods of the Invention

A method according to the first aspect of the invention may optionally further comprise selecting a suitable treatment regimen in the event that the subject is diagnosed as having kidney disease.

A method according to the first aspect of the invention may optionally further comprise implementing a suitable treatment regimen in the event that the subject is diagnosed as having kidney disease. The implementation may comprise prescribing the selected treatment regimen. Alternatively, the implementation may comprise providing the selected treatment regimen to the subject.

A suitable treatment regimen in the context of the preceding paragraphs may employ the medical use of binding partners for an anti-IQCJ antibody in accordance with the fourth aspect of the invention, a method of preventing or treating kidney disease in accordance with the fifth aspect of the invention, or the use of a device for extracorporeal treatment of a patient's blood in accordance with the sixth aspect of the invention.

Similarly methods in accordance with the second aspect of the invention may optionally further comprise implementing a suitable prevention or treatment regimen that has been selected by the method of the invention. As above, the implementation may comprise prescribing the selected treatment regimen or providing the selected treatment regimen to the subject. A suitable treatment regimen may employ the medical use of binding partners for an anti-IQCJ antibody in accordance with the fourth aspect of the invention, a method of preventing or treating kidney disease in accordance with the fifth aspect of the invention, or the use of a device for extracorporeal treatment of a patient's blood in accordance with the sixth aspect of the invention.

The methods of the first, second, or third aspects of invention may further comprise assessment of one or more additional markers indicative of kidney disease. Such additional markers may be conventional in the art, or may be new markers. Methods utilizing combinations of markers may, for example, increase the number of different forms of kidney disease that may be diagnosed by the methods of the invention. Merely by way of example, such additional markers may include antibodies that react with podocyte proteins. Suitably, such additional markers may include one or more markers selected from the group consisting of: anti-PLA2R antibodies; anti-nephrin antibodies; and anti-podocin antibodies.

Prevention or Treatment of Kidney Disease

The present disclosure, addresses the prevention or treatment of kidney disease in a number of contexts: including selection or monitoring of treatment regimens for the prevention or treatment of kidney disease; methods of preventing or treating kidney disease; and medical uses for the prevention or treatment of kidney disease.

Except for where the context requires otherwise, a reference to "treatment" of kidney disease in the present specification should be taken as directed to any effective intervention which has as its purpose the aim of alleviating a disorder manifesting itself as a clinically discernible disease. Treatment, in this context, may encompass any intervention which leads to symptoms of a kidney disease being reduced, or any intervention that prevents the symptoms of kidney disease from worsening in the manner that may be expected if no treatment is undertaken.

For purposes of understanding the present disclosure, references to "prevention" of kidney disease should be taken as directed to intervention initiated before clinical symptoms manifest themselves. Thus methods of preventing kidney disease will be those that avoid the development of clinical symptoms. It will be appreciated that the diagnostic methods of the invention may be of particular benefit in allowing detection of kidney disease before any clinical symptoms are manifest, thereby permitting the use of methods of the invention in order to prevent kidney disease developing.

The prevention or treatment of kidney disease in may be practiced using binding partners for anti-IQCJ antibodies, and such binding partners are discussed further below.

Methods of prevention or treatment, medical uses, or devices of the invention may make use of binding partners for anti-IQCJ antibodies as the sole therapeutic agent, or as part of a combination therapy. Suitably such combinations may include immunosuppressive drugs as additional therapeutic agents. Examples of such additional therapeutic agents may be selected from the group consisting of: steroids; cyclophosphamide; cyclosporine; and anti B cell monoclonal antibodies. The binding partners for anti-IQCJ antibodies may be provided preceding, at the same time as, or following treatment with additional therapeutic agents such as immunosuppressive drugs.

Binding Partners

Certain aspects of the invention make use of binding partners for anti-IQCJ antibodies. The role of such binding partners is to bind to, and thus reduce the adverse impact of, anti-IQCJ antibodies. Any suitable binding partner capable of achieving this activity may be used Suitably, binding partners may neutralize anti-IQCJ antibodies (for example by binding to the antibody in a manner that prevents the antibody binding to further IQCJ in the subject), or may reduce the amount of the anti-IQCJ antibodies present in the subject. .

Suitably, the binding partners utilized will have a preferential affinity for anti-IQCJ antibodies as opposed to other antibodies that may be present. Indeed, the binding partners may be specific for anti-IQCJ antibodies, which is to say that they exhibit minimal, or preferably substantively no, binding of antibodies other than anti-IQCJ antibodies.

A suitable binding partner may comprise an epitope recognized by the anti-IQCJ antibodies to which it is to bind.

In a suitable embodiment the binding partner may comprise a polypeptide comprising an epitope for an anti-IQCJ antibody. By way of example, such a polypeptide may comprise an antibody-binding portion of IQCJ. Such an antibody-binding portion of IQCJ may be provided in the form of the complete IQCJ sequence set out in SEQ ID NO:1. Alternatively, the antibody-binding portion of IQCJ may be provided in the form of a fragment of the IQCJ sequence set out in SEQ ID NO:1. A fragment may comprise 6 or more contiguous amino acid residues of SEQ ID NO:1; optionally 15 or more contiguous amino acid residues of SEQ ID NO:1; suitably 25 or more contiguous amino acid residues of SEQ ID NO:1; or 50 or more contiguous amino acid residues of SEQ ID NO:1.

Alternatively, a suitable binding partner for an anti-IQCJ antibody may be a variant of the IQCJ sequence set out in SEQ ID NO:1, or a fragment thereof Such a variant may differ from the sequence of SEQ ID NO:1, or a fragment thereof, such that the variant shares at least 99% identity, at least 98% identity, at least 97% identity, at least 96% identity, at least 95% identity, at least 94% identity, at least 93% identity, at least 92% identity, at least 91% identity, or at least 90% identity with the sequence of SEQ ID NO:1 (or a fragment of this sequence from which the variant is derived). Alternatively a suitable variant may share at least 85% identity, at least 80% identity, at least 75% identity, or at least 70% identity, with the sequence of SEQ ID NO:1 (or a fragment of this sequence from which the variant is derived).

Polypeptide binding partners may comprise recombinant IQCJ, such as recombinant human IQCJ, or fragments or variants thereof In a suitable embodiment, a polypeptide binding partner may take the form of a fusion protein comprising multiple (two, three, four, five, or more) joined epitopes for an anti-IQCJ antibody.

Medical Uses of Binding Partners for Anti-IQCJ Antibodies

The invention provides binding partners for anti-IQCJ antibodies for use in the prevention or treatment of kidney disease as its fourth aspect. As discussed above, a binding partner of this sort may comprise IQCJ, or a fragment or derivative thereof. A binding partner for use in accordance with this aspect of the invention may be provided to a subject requiring such prevention or treatment in a therapeutically effective amount.

In a suitable embodiment, a therapeutically effective amount of a binding partner for anti-IQCJ antibodies is an amount of such a binding partner that provides a therapeutically effective inhibition of binding of anti-IQCJ antibodies to native IQCJ in the subject.

The skilled person will be able to determine a therapeutically effective amount of an anti-IQCJ antibody binding partner by a range of measures conventional to this field of the art. Merely by way of example, test amounts of a binding partner for an anti-IQCJ antibody may be provided to the subject, and the effectiveness of these various treatment regimens established by a method in accordance with the third aspect of the invention.

In a suitable embodiment, a binding partner for an anti-IQCJ antibody for medical use in accordance with the invention (for example in the methods for prevention or treatment of kidney disease in accordance with the fifth aspect of the invention) may be provided in a form that is adapted to allow the binding partner, and anti-IQCJ antibodies associated with the binding partner, to be retained.

Suitably, a binding partner adapted in this manner may be associated with a retention moiety, such as a magnetic bead or the like.

Alternatively, the binding partner may be adapted by immobilization on a substrate. Suitably, such a substrate may be part of an immunosorbent column. Further details of such embodiments are described elsewhere in this disclosure.

The inventors believe that binding partners for anti-IQCJ antibodies have not previously been proposed as having medical utility, and so the invention also provides, in a further aspect, a binding partner for an anti-IQCJ antibody for use as a medicament. The binding partner may comprise IQCJ, or a fragment or derivative thereof.

Methods of Prevention or Treatment of Kidney Disease

The fifth aspect of the invention provides methods of preventing or treating kidney disease in a subject, these methods involving the production of an antibody-depleted volume of blood. The depletion of antibodies from the blood removes agents that cause kidney damage, and the resultant lack of damaging antibodies in the subject's circulation enables the prevention or treatment of kidney disease.

The volume of antibody-depleted blood is, in due course, provided to the subject of the treatment. The blood may be returned immediately to the subject, as considered further below, or may be stored prior to administration to the subject.

There are many different ways in which the step of contacting the volume of the subject's blood with a binding partner for an anti-IQCJ antibody may be practiced, and suitable examples of these will be readily apparent to those skilled in the art. For instance, the contacting step may be practiced extracorporeally, suitably using a device for extracorporeal treatment of a patient's blood in accordance with the sixth aspect of the invention.

In a suitable embodiment, a batch of blood comprising one or more volumes of blood to be treated is removed from the subject, and the steps of contacting a volume of the blood with the binding partner, and subsequent separation of the binding partner and bound antibodies, completed to yield a batch comprising the volume, or volumes, of antibody-depleted blood. Some, or all, of the batch of blood may then be returned to the patient. Alternatively, some or all, of the batch of blood may be stored before return to the patient.

In an alternative embodiment, the steps of contacting the blood with the binding partner, and subsequent separation, are carried out "in line". Suitably the binding partner is provided in an arrangement so that the patient's blood may flow over the binding partner, thus allowing it to bind anti-IQCJ antibodies in the blood. Continued flow of blood then causes separation of the blood from the retained antibody-binding partner complex, to yield an antibody-depleted volume of blood. The antibody-depleted volume of blood may then be returned directly to the patient, or retained for future use, as above.

It will generally be that case that the subject from whom the blood has been taken will be the subject requiring the prevention or treatment of kidney disease.

Devices for Extracorporeal Treatment of a Patient's Blood

Devices of the sixth aspect of the invention incorporate means for separating a binding partner for an anti-IQCJ antibody from blood, and such devices represent a suitable embodiment that may be employed in the methods of the fourth aspect of the invention.

Suitable means for separating the binding partner from the blood may comprise immobilizing means. Such immobilizing means may comprise a substrate to which the binding partner is attached. In such embodiments passage of blood over the substrate to which the binding partner is attached will allow antibodies present in the blood to attach to the binding partner, and the substrate will retain the binding partner and bound antibody in place. Relative movement of the blood and immobilized binding partner serves to separate antibodies bound to the binding partner from the blood.

Alternatively, the immobilizing means may comprise a retention moiety, such as a magnetic bead or the like, coupled to the binding partner. In this case, the retention moiety may allow immobilization of the binding partner, and thus separation of the bound antibodies from the blood.

Suitable examples of substrates to which a binding partner may be attached, and thus immobilized, in devices of the sixth aspect of the invention include those used in immunosorbent columns. Merely by way of example, suitable substrates to which a binding partner for an anti-IQCJ antibody may be attached include those selected from the group consisting of: cellulose; cellulose derivatives; agarose; agarose derivatives; polysulphone; polysulphone derivatives; polyacrylamide; polyacrylamide derivatives; and nylon. Such substrates may optionally be provided in forms including hollow fibre cassettes, membranes, or beads. In view of the above, it will be appreciated that immunosorbent columns comprising suitable substrates, such as those constituents or forms listed above, represent preferred embodiments of the devices of the sixth aspect of the invention.

In a suitable embodiment a device for extracorporeal treatment of a patient's blood in accordance with the sixth aspect of the invention incorporates a polypeptide comprising IQCJ (SEQ ID NO:1), or a fragment or variant thereof, as the binding partner for an anti-IQCJ antibody. In a suitable embodiment the polypeptide comprising IQCJ, or fragment or variant thereof is immobilized on a substrate within an immunosorbent column. Accordingly, it will be recognized that immunosorbent columns represent suitable embodiments of the devices of the invention.

The methods, medical uses, and devices of the invention are suitable for use in a range of subjects. Kidney disease afflicts not only human subjects, but also animals including domestic cats and dogs. Except for where the context requires otherwise, a suitable subject may generally be selected from the group consisting of: a human subject, a feline subject, and a canine subject.

The invention will now be further described, with reference to the accompanying examples and drawings, in which: FIG. 1 shows a table illustrating pedigree for a family with incidences of kidney disease associated with anti-IQCJ antibodies; and histology using light and electron microscopy to investigate tissue associated with this disease; FIG. 2 sets out details of deletions on Chromosome 3 associated with kidney disease; and immunolabelling of IQCJ in histology samples; FIG. 3 shows electron microscopy images; and the results of methods detecting anti-IQCJ antibodies in human sera; FIG. 4 illustrates results obtained in genetically manipulated zebrafish; and FIG. 5 shows results of studies investigating localisation of IQCJ expression and protein.

Example 1

Study Participants

The index family was a consanguineous British Pakistani family with two siblings affected by early on-set end-stage renal disease (ESRD). Ethical approval for this study was obtained from the University of Manchester (06138) and NHS ethics committees (06/Q1406/52). Informed consent was obtained from all participating individuals. Serum samples from 42 patients with anti-PLA2R positive IMN and 3 patients with anti-PLA2R negative de novo MN were obtained from the Manchester Renal Biobank (10/H1008/10).

Study Design and Investigations

Whole genome linkage analysis was performed in the index family using the Affymetrix SNP6.0 array. The deletion was confirmed by polymerase chain reaction (PCR) and breakpoints delineated by Sanger sequencing. The 5500 SOLiD platform (Life Technologies, Applied Biosystems) was used for whole exome sequencing and sequence variants were compared to the human reference genome (version GRCh37/Hg19). Variants were screened for association with renal disease. IQCJ and the hybrid transcript IQCJ-SCHIP1 were identified as a target regulated by the deleted sequence using transcriptional bioinformatics. Post-transplant sera from cases 1 and 2, both negative for anti-PLA2R, were screened for antibodies using customized ELISA developed using recombinant human IQCJ and SCHIP1 (discussed further below). In addition, sera from 3 de novo MN cases and 42 anti-PLA2R positive MN cases were screened for anti-IQCJ. The functional effects of deleting IQCJ or SCHIP1 were tested in a zebrafish morpholino knockdown system. The presence of edema was scored and the integrity of the glomerular filtration barrier was assessed by electron microscopy and indirectly measured by quantifying a fluorescently labelled high molecular weight protein in the circulation. Expression and localization of endogenous IQCJ and SCHIP1 were investigated in human podocytes.

Experimental Details of ELISA for Detection of Anti-IQCJ Antibodies

Recombinant IQCJ protein was coated at 1 ug/ml (100 ul) in bicarbonate buffer pH 9.6 overnight. Following blocking with Superblock for 1 hour, patient sera diluted 1/50 in Superblock plus 0.05% Tween 20 was incubated with plate shaking for 2 hours. Following washing in PBS Tween, peroxidase anti-human IgG 1: 25,000 was added to the wells and incubated with shaking for 2 hours. After the final washing stage, the peroxidase activity was detected using TMB (Sigma Aldrich Poole UK) and absorbance A450 measured in a spectrometer after addition of $H_2SO_4$ at 10 mins. The normal range of reactivity of serum from healthy individuals was established in the assay and by setting the normal range at mean plus 3SDs, values above this are deemed positive for anti-IQCJ antibodies.

Patients and Clinical Phenotype

Referring now to FIG. 1A, the index family was a consanguineous British Pakistani family with two siblings affected by early onset end stage renal disease (ESRD). The proband (Case 1) presented with ESRD aged 15 years whilst her older brother (Case 2), presented aged 25 years.

Figure 1B:
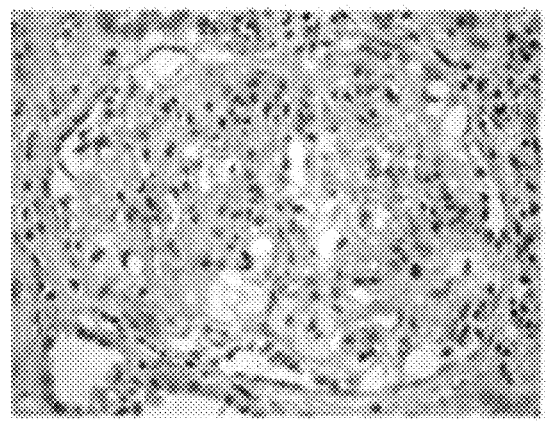
FIG. 1B. Photograph showing Haemotoxylin and eosin staining of a native renal biopsy from Case 2.
Figure 1C:
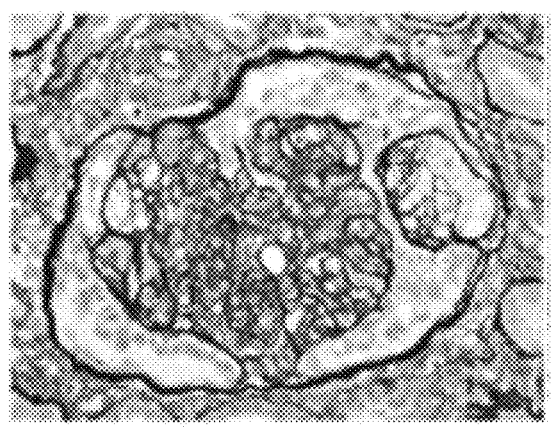
FIG. 1C. Photograph showing silver staining of a native renal biopsy from Case 2.
Figure 1D:
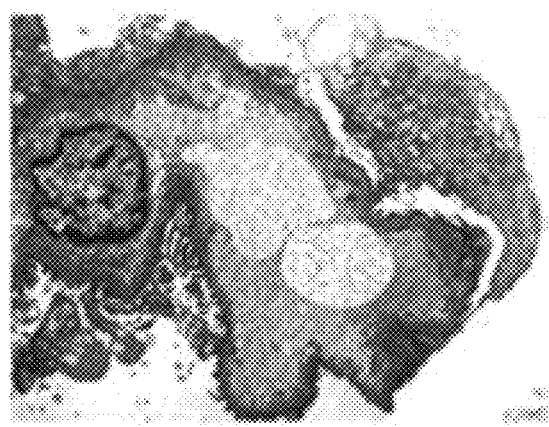
FIG. 1D. Electron microscopy showing moderate effacement of podocyte foot processes.

The siblings had similar facial dysmorphism. Their mother (Case 3) presented with ESRD aged 50 years and their father (Case 4), presented with CKD 3 aged 60 years. Native renal biopsy was performed on Case 2. Referring now to FIG. 1B, the biopsy showed severe chronic damage with 80% tubular atrophy. There were 4 glomeruli, one globally sclerosed and two showing advanced segmental sclerosis and hyalinosis. There was marked podocyte hypertrophy and hyperplasia, and prominent endocapillary foam cells. Referring now to FIG. 1C, there was no evidence of membrane spikes on silver staining Immunohistochemistry showed positivity for IgM and C3 in capillary walls and hyalinotic lesions, interpreted as non-specific trapping. IgG and IgA were negative. Referring now to FIG. 1D, electron microscopy showed moderate effacement of podocyte foot processes and abundant lipid within Bowman's basement membrane. There was no evidence of electron dense deposits. These findings exclude the possibility of MN as the primary renal disease and are indicative of a primary podocytopathy. Cases 1 and 2 underwent cadaveric renal transplantation and developed aggressive de novo MN, characterized by the sub-epithelial electron dense deposits (FIGS. 3A and 3B) and rapid early graft failure.

Genetic and Bioinformatics Studies

Figure 1E:
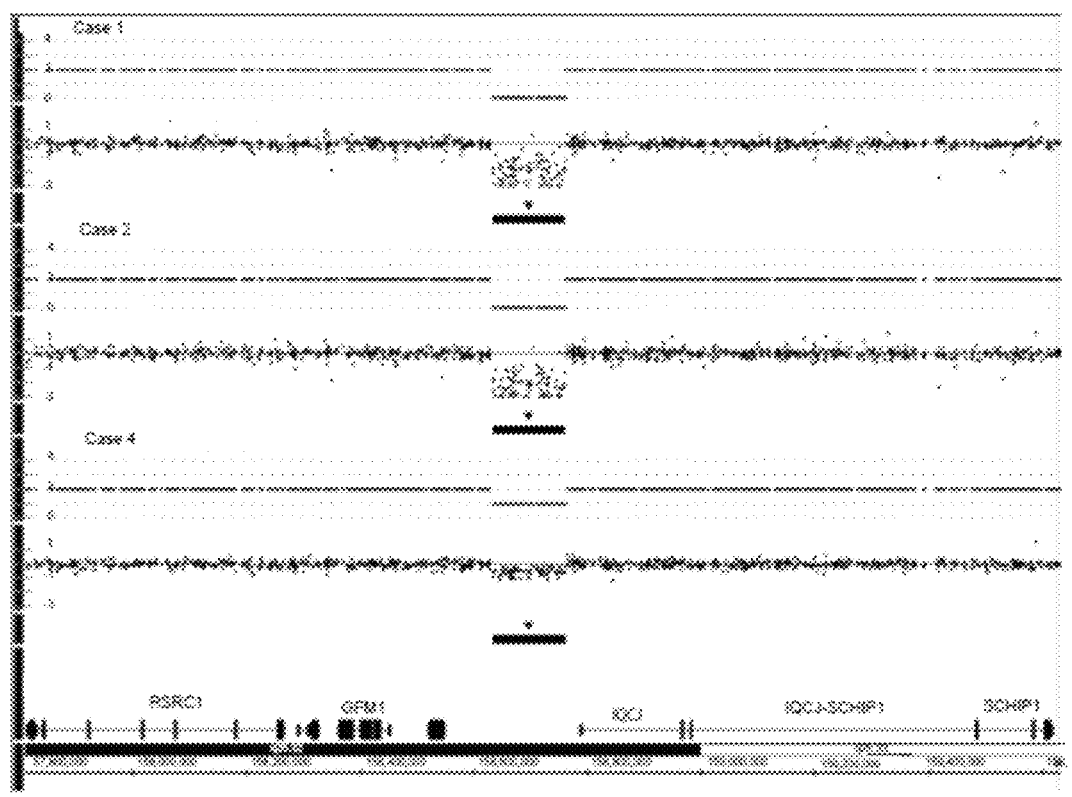
FIG. 1E. Array copy number analysis showing a homozygous deletion between 158,000,000 and 159,000,000 on Chromosome 3 in Cases 1 and 2.
Figure 2A:
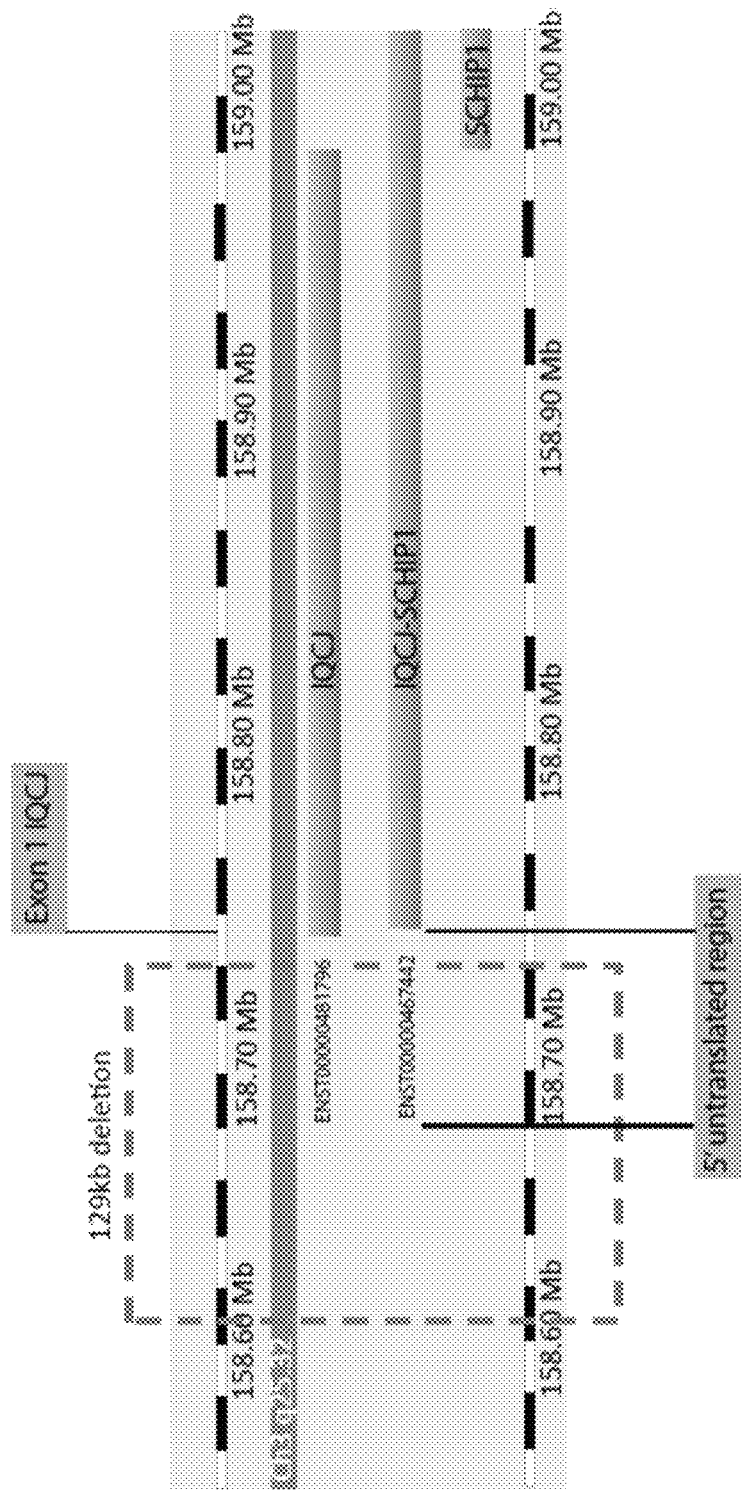
FIG. 2A. Schematic diagram showing the deleted region on Chromosome 3 encodes two non-coding RNA transcripts for IQCJ and IQCJ-SCHIP1 (ENST00000481796 and ENST00000467442 respectively).

Autozygosity mapping revealed five significant homozygous regions shared by Case 1 and 2 but not Case 6. Referring now to FIG. 1E, within one region on chromosome 3, array copy number analysis identified a homozygous deletion between 158,000,000 and 159,000,000 in Cases 1 and 2. The deletion was heterozygous in case 3, 4 and 6. Sanger sequencing confirmed the deletion between the coordinates 158,631,856 and 158,761,201 on chromosome 3 (129, 545bp, GRCh37/Hg19). The deletion occurred 25,840bp before exon 1 of IQCJ. Referring now to FIG. 2A, exome sequencing did not find any alternative genetic cause due to genes known to cause podocytopathy. Bioinformatics analysis of the deleted sequence identified two non-coding RNA sequences connecting the deletion to IQCJ and the hybrid transcript IQCJ-SCHIP1 and therefore IQCJ was selected for further investigation.

IQCJ Tissue Expression

Figure 2B:
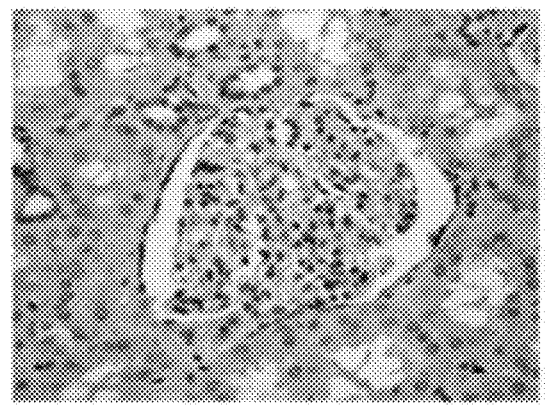
FIG. 2B. Photograph of histology sample showing secondary antibody staining alone.
Figure 2C:
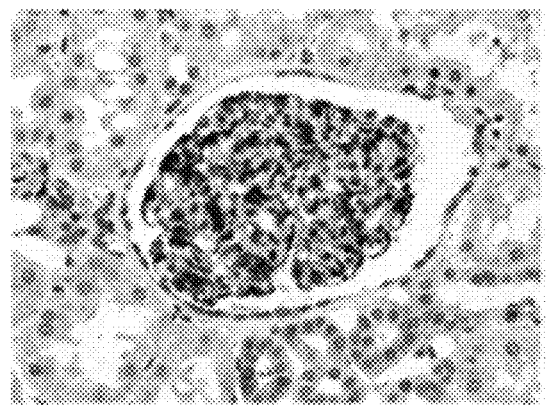
FIG. 2C. Photograph of histology sample showing IQCJ staining.
Figure 2D:
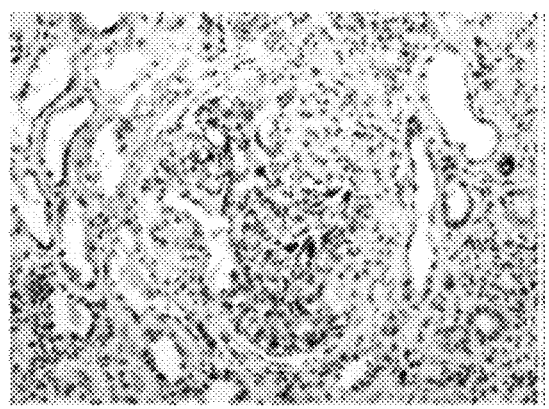
FIG. 2D. Photograph of the biopsy from Case 2 showing IQCJ staining in non-sclerosed regions FIG. 3A. Electron microscopy showing the appearance of the transplant in Case 1.

Referring now to FIG. 2B, in normal human glomeruli the immunodetection of IQCJ was confined to the cytoplasm of podocytes. In glomeruli from Case 2, IQCJ was detected in a podocyte-cytoplasmic distribution but was absent in areas of segmental sclerosis (FIG. 2C). Referring now to FIG. 2D, dual immunohistochemistry with the podocyte membrane maker nephrin and IQCJ, revealed colocalization in a subset of podocytes and the expression pattern was suggestive of a cytoplasmic localization.

IQCJ Autoantibodies Associate with Membranous Nephropathy

Figure 3A:
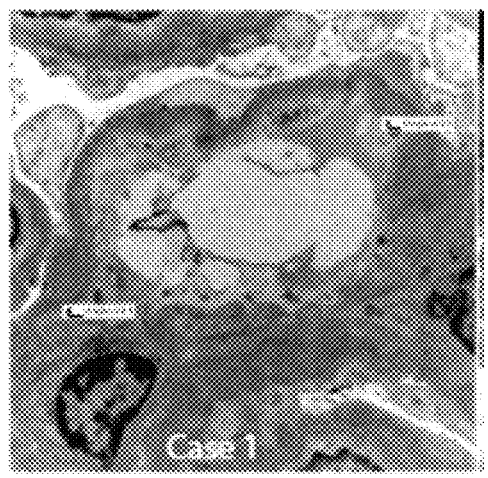
FIG. 3B. Electron microscopy showing the appearance of the transplant in Case 2.
FIG. 3C. Graph showing anti-IQCJ antibody levels measured over time from first transplantation, during dialysis and during 2nd transplant in Case 1.
FIG. 3D. Graph showing anti-IQCJ antibody levels measured over time from first transplantation, during dialysis and during 2nd transplant in Case 2.
FIG. 3E. Graph showing the presence of anti-IQCJ antibodies from patients with MN and normal controls.
Figure 3B:
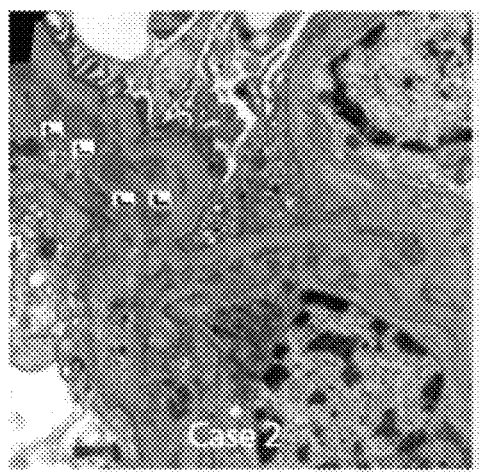
Figure 3C:
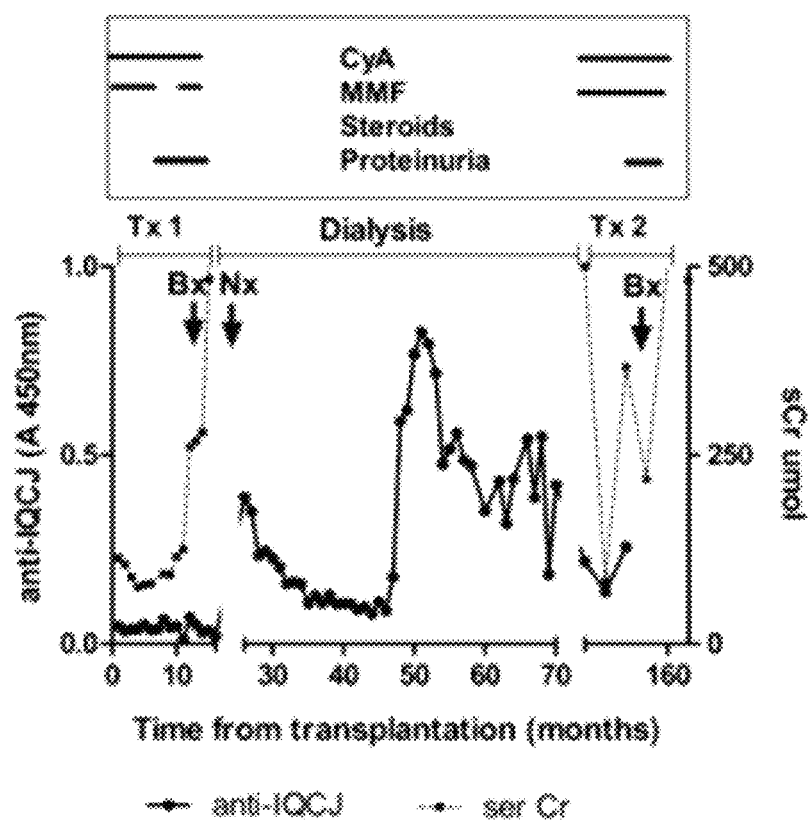
Figure 3D:
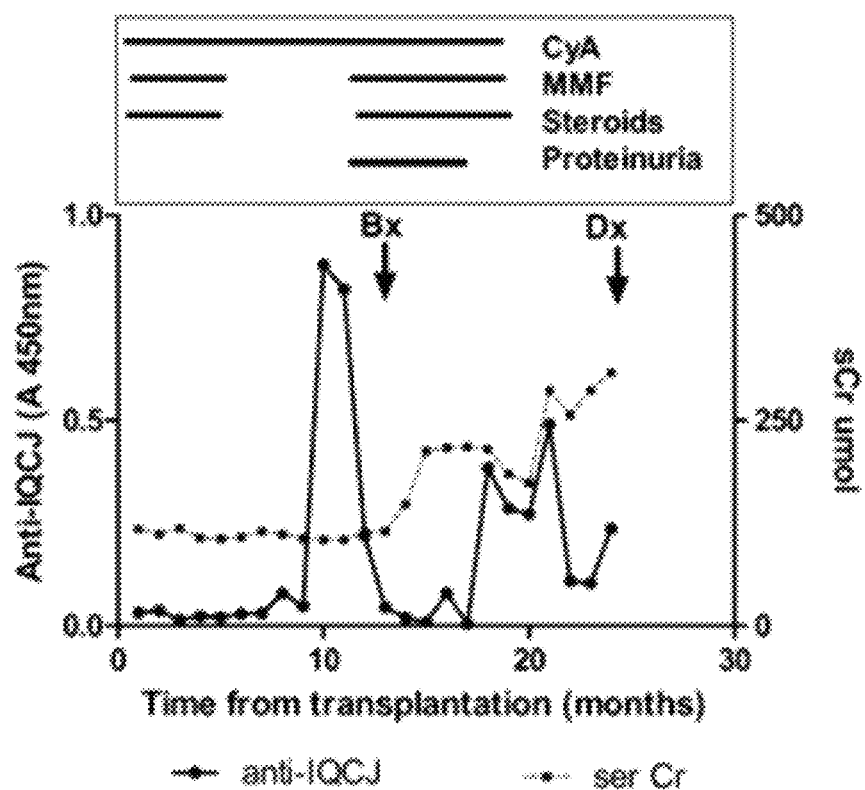

Referring now to FIG. 3, Cases 1 and 2 developed MN post-transplantation (FIGS. 3A and 3B) and monthly sera from pre-transplant to graft failure were screened for antibodies to IQCJ, SCHIP-1, and PLA2R (FIGS. 3C and 3D). No antibodies to SCHIP-1 or PLA2R were detected in any samples (data not shown). Anti-IQCJ antibodies were detected post transplantation in both cases with a different temporal pattern in relation to onset of clinical events of proteinuria and graft dysfunction. In Case 1, anti-IQCJ was only detectable in serum after graft failure, nephrectomy and cessation of immunosuppression and the patient remained seropositive for over 10 years on dialysis until the time of the second transplant. This second allograft showed accelerated loss of function within 3 months due to de novo MN. In Case 2, anti-IQCJ was detected and this was coincident with onset of proteinuria and biopsy classification of de novo MN. The anti-IQCJ titre reduced with increased immunosuppression but showed rebound prior to graft loss.

Figure 3E:
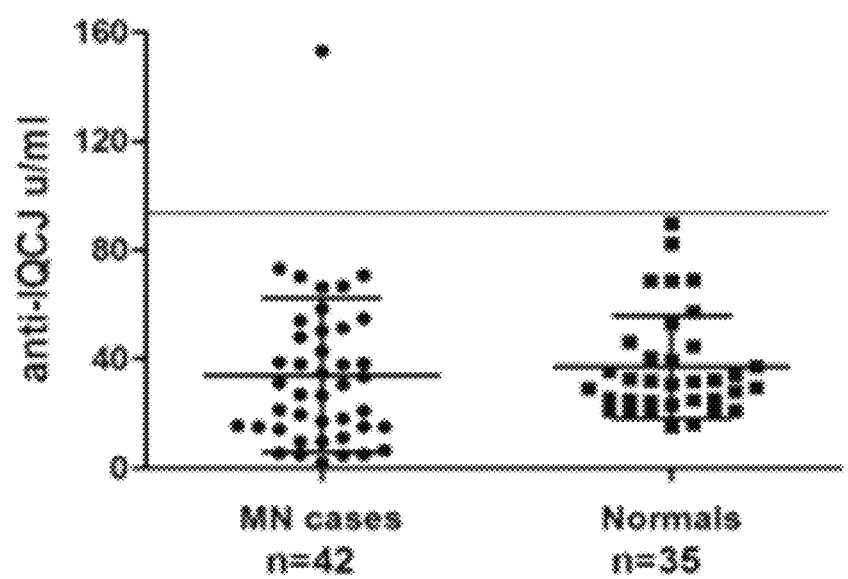
Figure 4A:
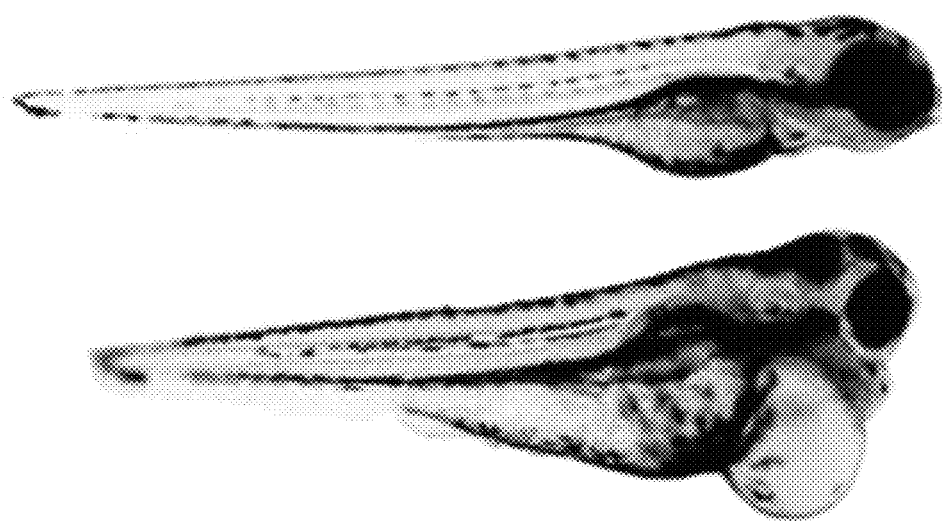
FIG. 4A. Photographs showing a control morpholino injected zebrafish and an IQCJ-knockdown (IQCJ$^{KD}$) zebrafish.
Figure 4B:
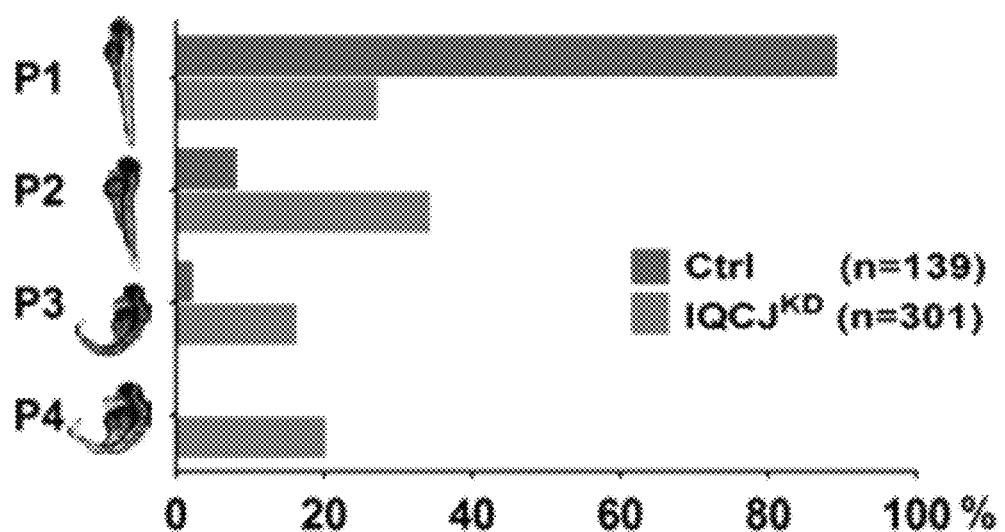
FIG. 4B. Bar graph showing the phenotype development after injection with a control (blue bars) or IQCJ specific splice-donor morpholino (orange bars) at 120 hours post fertilization (hpf). Edema development was graded as P1=no phenotype, P2=mild phenotype, P3=severe and P4=very severe phenotype.
Figure 4C:
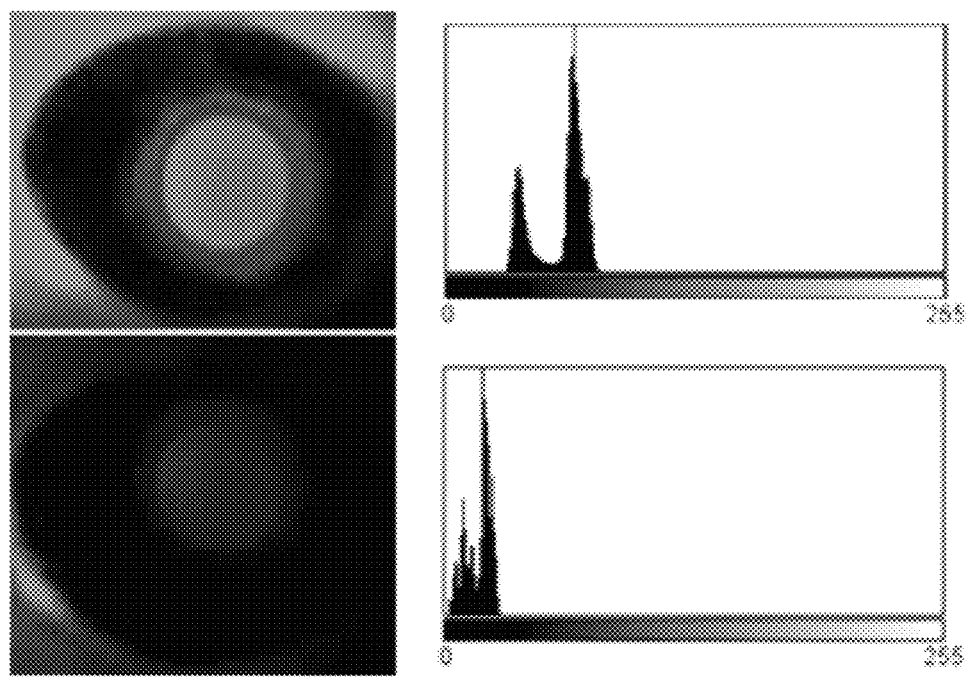
FIG. 4C. Photographs showing Tg (1-fabp:DBP-EGFP) transgenic zebrafish develop increasing systemic fluorescence with circulating EGFP labelled Vitamin-D binding protein (MW ~78 kDa), which was monitored over the retinal blood vessels at 120 hpf.
Figure 4D:
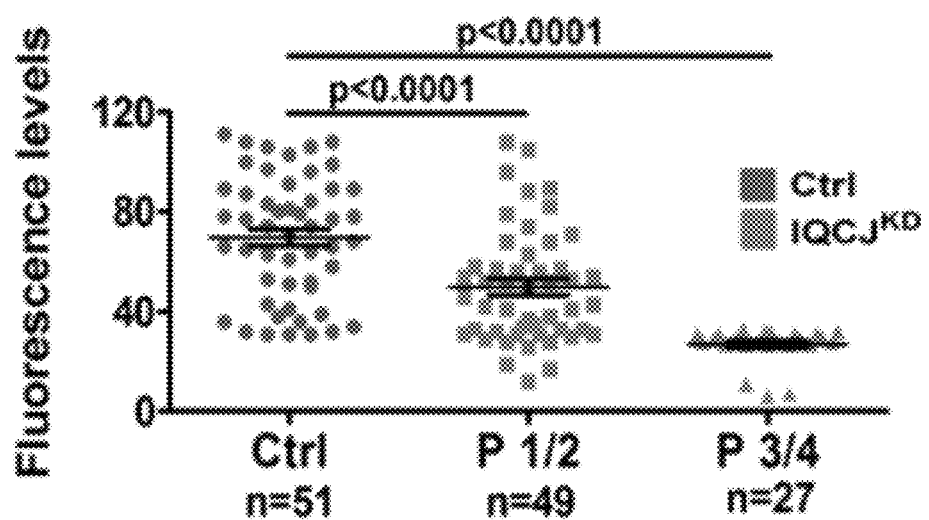
FIG. 4D. Graph showing the effect of IQCJ$^{KD}$ in systemic fluorescence in mild (P1/2) (orange squares) and severely affected (P3/P4) (orange triangles) phenotypes of knockdown fish compared to the control (blue circles).
Figure 4E:
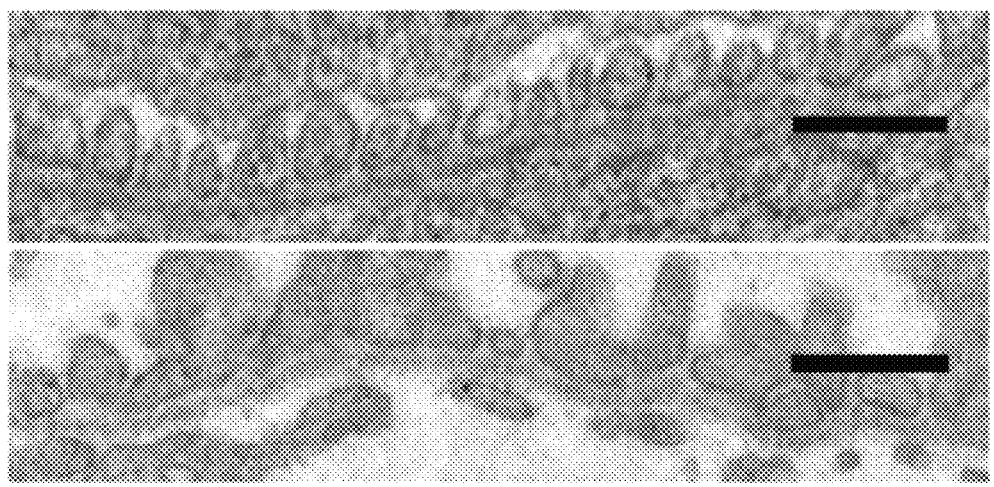
FIG. 4E. Transmission Electron Microscopy (TEM)-analysis showing the effect of podocyte foot processes in control morpholino injected embryos and in IQCJ$^{KD}$ embryos (size bar=500 nm).
Figure 4F:
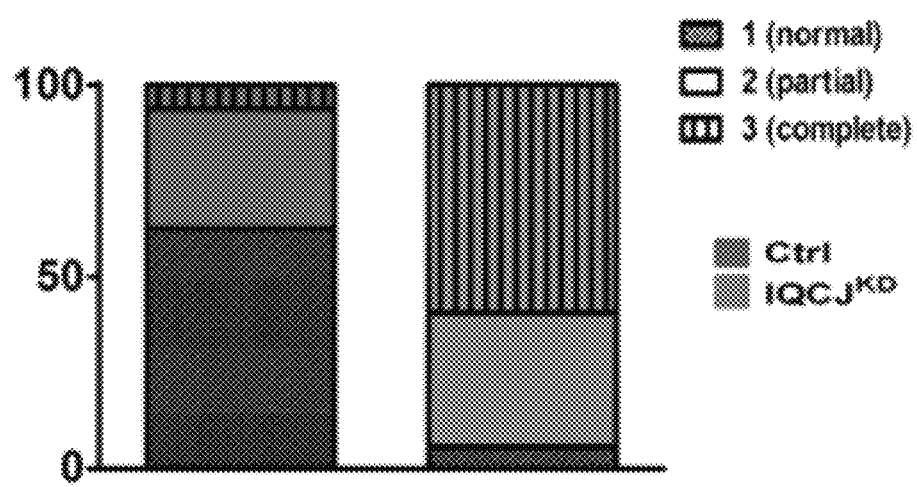
FIG. 4F. Bar graph showing quantification of foot effacement in control (blue, Ctrl) and in IQCJ$^{KD}$ (orange).

Referring now to FIG. 3E, Sera from patients with idiopathic membranous nephropathy (IMN) were screened for the presence of PLA2R [12] and IQCJ antibodies. 1/42 cases (2.4%) of anti-PLA2R positive and 0/3 anti-PLA2R negative de novo IMN cases were shown to contain anti-IQCJ antibodies.

Functional Genomics

Referring now to FIG. 4, a splice-donor morpholino specific for the IQCJ zebrafish orthologue and a scrambled control were injected in fertilized zebrafish eggs and the development of edema was monitored for up to 120 hours post fertilization (hpf). At 120 hpf a large percentage of the IQCJ knockdown (IQCJ$^{KD}$) fish displayed a generalized edema phenotype compared to embryos injected with a scrambled control morpholino in the same concentration. Approximately 72% of embryos developed pericardial effusion as well as generalized swelling of the yolk sac (FIG. 4A). The edema was scored according to severity by defining phenotype 1 (P1) as normal, no edema; P2 as mild edema; P3 as severe and P4 as very severe edema. Referring now to FIG. 4B, more than 37% of fish were in the P3/P4 category with a severe to very severe phenotype indicating a renal phenotype in contrast to control morpholino injected fish from the same clutches with 90% normal phenotypes (phenotype 1). As an indirect measure of integrity of the glomerular filtration barrier we monitored the systemic fluorescence activity in the retinal vessels of the Tg (1-fabp: DBP-EGFP) transgenic fish model system, an assay system that we have used in the past to verify proteinuria development. This transgenic fish produces significant amounts of a circulating vitamin-D-binding protein fused to EGFP with a molecular weight of approximately 78 kDa. The transgene expression is driven by an FABP-promoter. While comparing accumulation of this endogenously produced marker in control-injected and IQCJ$^{KD}$-fish, a systemic loss of this high molecular weight protein in IQCJ$^{KD}$-fish was documented (FIG. 4C). Referring now to FIG. 4D, interestingly, a significant loss of circulating high molecular weight fluorescence DBP-EGFP was found in severely (P3/P4-phenotypes) but also in mildly affected (P1/P2-phenotypes) IQCJ$^{KD}$-fish. Referring now to FIG. 4E, transmission electron microscopy (TEM) revealed fusion and effacement of the podocyte foot processes (hallmark of human FSGS/ nephrotic syndrome) in the IQCJ -fish compared to control morpholino injected fish. The structure of the GBM and the fenestration of the endothelium appeared normal. In order to quantify the podocyte damage, 500nm increments of the filtration barrier were rated as score 1:normal appearing, pearl-string like foot processes, score 2: partially effaced, only 1 filtration slit visible or score 3: complete effacement. Referring now to FIG. 4F, when a total of 67.5 μm of glomerular capillary loops in control and 97.5 μm of glomerular capillary loops in IQCJ$^{KD}$-fish were rated using this analysis, more than 60% of effacement in the IQCJ$^{KD}$-fish compared to 60% pearl string like appearance in the control injected fish were detected. Comparable experiments inducing a knockdown of SCHIP-1 expression did not induce a phenotype in zebrafish (data not shown). These data indicate a significant loss of high molecular weight proteins from the circulation in the absence of functional IQCJ in this in vivo proteinuria model and demonstrate a disruption of the glomerular filtration barrier specifically with a clear podocyte phenotype on TEM.

IQCJ Links to Autophagy Pathways in Human Podocytes

Figure 5A:
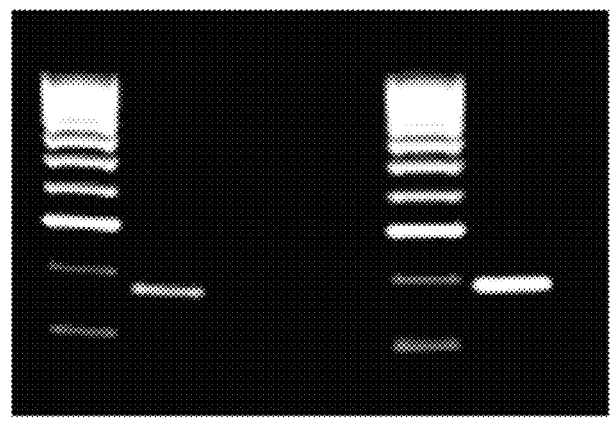
FIG. 5A. Electrophoresis showing the expression of mRNA of IQCJ and SCHIP1 in conditionally immortalized human podocytes.
Figure 5B:
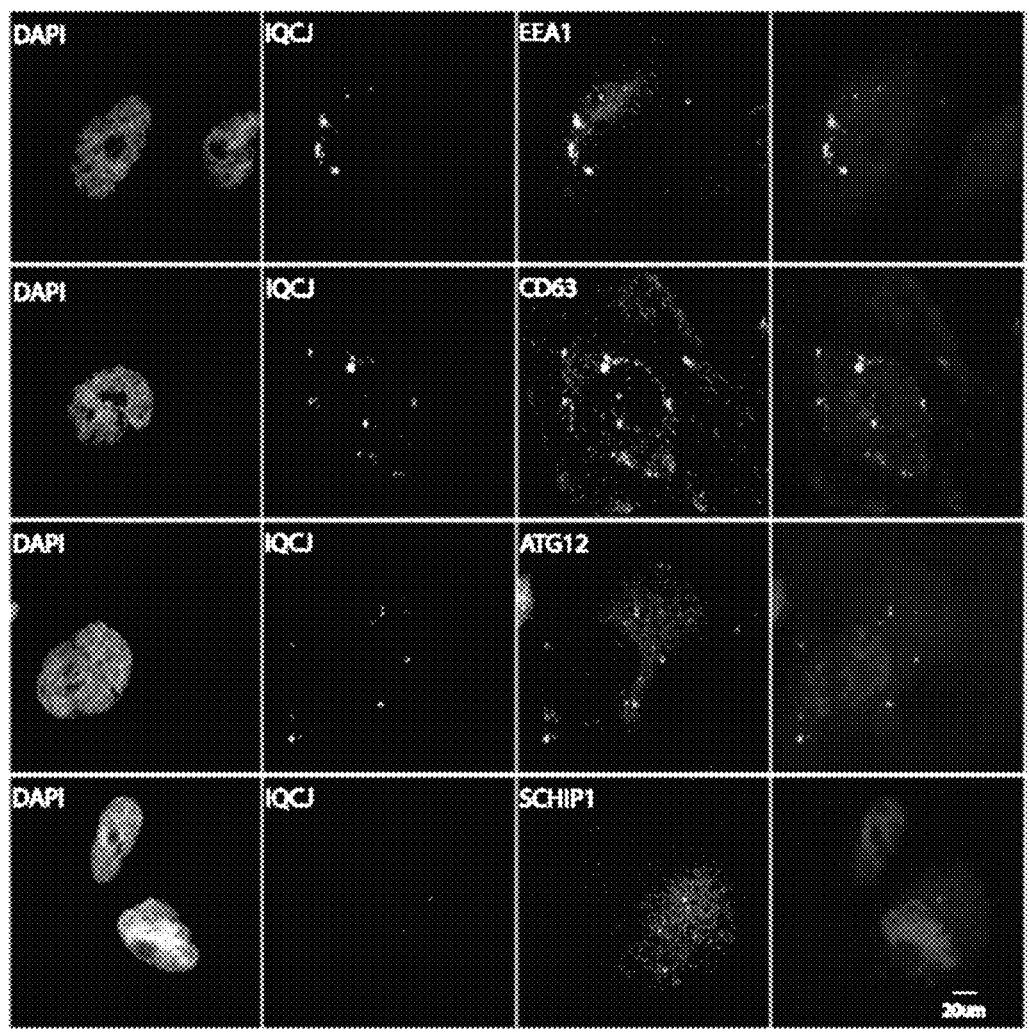
FIG. 5B. Photographs of podocytes showing the colocalization with the early endosomal marker EEA1, the lysosomal marker CD63, the marker of autophagosomes ATG12 and with SCHIP-1.

Human podocytes were investigated for endogenous expression of IQCJ and SCHIP1. Referring now to FIG. 5A, mRNA transcripts for both IQCJ and SCHIP-1 were demonstrated in cultured podocytes by PCR. FIG. 5B demonstrates that IQCJ protein localized within large vesicular structures in the cytoplasm. These structures were not present in all cells and were more evident in differentiated compared to proliferating podocytes. There was colocalization with SCHIP1, which had a more diffuse, vesicular pattern and further colocalization with endosomal markers EEA1, CD63 and Rab11 (data not shown). There was no colocalization with actin stress fibres or the focal adhesion protein paxillin (data not shown). The large vesicles resembled autophagosomes and IQCJ colocalized almost completely with the autophagy protein ATG12 (data not shown).

Discussion

A novel 129 kb deletion on chromosome 3, adjacent to IQCJ was identified as a single copy deletion in parents and as a homozygous deletion in the two affected siblings. The parents demonstrated a variable phenotype, mother presenting in renal failure at age 50 and father diagnosed with CKD at age 60. Only the two affected children experienced the severe phenotype with presentation at CKD 5 at ages 15 and 25 yrs and a similar temporal aggressive de novo MN course post transplantation resulting in graft loss within 2 years. This is consistent with a complex autosomal recessive trait showing a dominant effect in siblings with homologous deletion. The analysis of the native biopsy from Case 2 excluded MN as the primary lesion and was suggestive of an advanced segmental and global glomerulosclerosis with podocyte hypertrophy and hyperplasia, consistent with a podocytopathy. Exome screening of Case 2 failed to identify any known genetic causes of podocytopathies.

IQCJ was identified as a partner in a novel human fusion gene IQCJ-SCHIP1 in 2006 in the context of genetic investigations in an individual with a 3q25-q29 inversion and language delay. Human fusion gene transcripts, where two adjacent independent genes in the same orientation merge into a single contiguous RNA transcript, are rare in comparison to prokaryote operons. Exploration of IQCJ-SCHIP1 expression in studies on human tissue identified two transcripts predominantly in fetal and adult brain and incidentally in kidney. In cultured neuronal cells IQCJ-SCHIP1 interacts with calmodulin through the conserved IQ domain and has been shown to align to actin filaments in neurite extensions.

Using an antibody specific to the C terminus of IQCJ (sequence not present in the IQCJ-SCHIP1 fusion protein), immunostaining on normal human kidney revealed that positivity was confined to podocytes Immunostaining of the native biopsy from Case 2 confirmed the presence of IQCJ protein specifically in podocytes with loss in segmental sclerosing lesions. Furthermore, we demonstrated expression of IQCJ and SCHIP1 but not a fusion transcript for IQCJ-SCHIP1 in normal human podocytes.

The gene deletion of 129 kb contains many transcriptional regulatory sequences e.g. TATA boxes identified by analysis of the sequence with bioinformatics. Furthermore it contains two non-coding RNA's, which link the deletion to both IQCJ and IQCJ-SCHIP-1. To test the functional role of IQCJ and SCHIP-1 we used morpholino knockdown of IQCJ and SCHIP-1 transcripts in zebrafish.

The IQCJ$^{KD}$ zebrafish developed an edematous phenotype, loss of high molecular weight proteins in the circulation as an indirect measure of proteinuria and foot process effacement. In contrast, SCHIP-1$^{KD}$ zebrafish did not develop a phenotype. The findings in the IQCJ$^{KD}$ zebrafish are similar to findings in patients with FSGS and other pathologic types of nephrotic syndrome. These data suggest that IQCJ plays a key role in the maintenance of the glomerular filtration barrier and indicate a specific functional role in podocytes.

We explored the location of IQCJ in normal human podocytes in culture using immunostaining with anti-IQCJ antibodies. The distinctive cytoplasmic staining was similar to that described for the neuronal expression of IQCJ-SCHIP1. Co-localization of IQCJ with a number of other cytoplasmic markers suggests a role in vesicle trafficking and autophagy.

In the last decade, a number of autosomal dominant and recessive forms of nephrotic syndrome have been explained by specific genetic defects affecting podocyte biology and function. A common consequence of the gene defects resulting in missing or aberrant podocyte proteins is a podocytopathy phenotype linked to $Ca^{2+}$ signaling pathways and/or interaction with the actin cytoskeleton clinically presenting as focal and segmental glomerulosclerosis (FSGS). The IQ motif with the general consensus sequence IQXXXRGXXXR binds to calmodulin (CaM). The IQ motif in the fusion protein IQCJ-SCHIP1 (conserved in IQCJ) interacts with CaM in the absence of $Ca^{2+}$ which suggests a role in $Ca^{2+}$ signaling. Our data from immunostaining of IQCJ in normal podocytes shows the protein associated with cytoplasmic vesicles which may regulate cytoskeletal organization. The IQCJ knockdown in zebrafish clearly demonstrates an effect on podocyte structure with loss of foot processes, consistent with modulation of the actin cytoskeleton De novo MN is a rare outcome of transplantation with a reported incidence of 2-6%. Despite recent progress in discovery of target antigens in idiopathic MN, alloimmune MN in pregnancy and in some pediatric cases, no antigen has yet been described in de novo MN. It has been reported that anti-PLA2R antibodies are not involved in 9 cases of de novo MN. Several mechanisms have been proposed to account for the pathophysiology of de novo MN cases including allogeneic immunization.

IQCJ is the first antigen to be identified as the cause of de novo MN through allogeneic immunization. However, we have shown that anti-IQCJ antibodies are also detectable in 1/42 IMN cases seropositive for anti-PLA2R. The temporal relationship between anti-IQCJ and anti-PLA2R and whether some of the 25% of IMN cases negative for anti-PLA2R might have anti-IQCJ antibodies is under investigation. Current knowledge of the mechanism of MN requires the podocyte target antigen to be expressed on the podocyte plasma membrane to provide a focus for autoantibody deposition. Antibody modulation of the antigen results in immune complexes being shed from the membrane and accreted in the sub-epithelial GBM as electron dense deposits. Therefore we tested the transplant biopsies for the presence of IQCJ co-staining with IgG in the immune complexes deposited in the capillary wall. A target antigen can be immunogenic in the post-transplant context if there is a significant allogeneic difference in donor antigen compared to the recipients as is seen in the production of DSA to HLA antigens. No DSA antibodies post-transplant were detected in easel and in case 2, the DSA were evident after nephrectomy but are not known to cause de novo MN. More likely is the possibility that the two cases never developed tolerance to IQCJ due to altered protein expression in their native kidneys. In the case of NHSP1, NHSP2 and COL4A3, 4, 5, the gene is disrupted and no protein is made. This is unlikely to be the case here as we see no disruption to exon coding and can demonstrate IQCJ protein in podocytes in the native glomeruli of Case 2. However, other possibilities exist for disruption of antigen expression necessary for establishing tolerance. Knockout of promotor function for IQCJ is likely in these cases and may result in significantly less antigen being made such that competition for limited antigen results in some functions of IQCJ being curtailed e.g cell surface expression. Containment of antigen within the cell, creating an effective site of immune privilege, might negate the development of natural immune tolerance.

The specific anti-IQCJ antibody production post transplantation reflects the host's abnormal lack of tolerance to IQCJ revealed by allogeneic immunization with a normal kidney with no antibodies reactive to SCHIP1. Similar allogeneic immunization has been reported post transplantation in other podocytopathies caused by genetic defects in NHSP 1 (nephrin), and COL4A (alpha 4 chain of Type IV collagen). The second transplant in Case 1 occurred whilst the patient was still seropositive for anti-IQCJ. The rapid accelerated graft loss due to recurrence of MN at 3 months implies the pathogenicity of anti-IQCJ antibodies.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

---

---

We claim:

1. A device for extracorporeal treatment of a patient's blood, the device comprising:
   a binding partner for an anti-IQCJ antibody, the binding partner comprising an epitope of IQCJ recognized by the anti-IQCJ antibody; bound to
   an insoluble structure, the insoluble structure including at least one material selected from the group consisting of: cellulose, cellulose derivatives, agarose, agarose derivatives, polysulphone, polysulphone derivatives, polyacrylamide, polyacrylamide derivatives, and nylon; and wherein the insoluble structure is attached to the binding partner.

2. The device according to claim 1, wherein the insoluble structure is selected from the group consisting of: hollow fibre cassettes, membranes, and beads.

3. A method of removing anti-IQCJ antibodies from blood, comprising the steps of: extracorporeally contacting a portion of a patient's blood with a binding partner for an anti-IQCJ antibody, the binding partner comprising an IQCJ epitope recognized by the anti-IQCJ antibody;
   retaining the binding partner that is bound to the anti-IQCJ antibody in the portion of the patient's blood;
   separating the binding partner and the bound anti-IQCJ antibody from the blood of the patient; and
   returning the blood to the patient.

4. The method according to claim 3, wherein said binding partner comprises at least one compound that has 100% identity with SEQ ID NO:1.

5. The method according to claim 4, wherein said binding partner further comprises a retention moiety selected from the group consisting of: a magnetic bead and a substrate.

6. The method according to claim 3, wherein the binding partner is provided in an arrangement so that the patient's blood may flow over the binding partner, thus allowing it to bind anti-IQCJ antibodies in the blood.

7. The method according to 3, wherein the contacting step, the retaining step, and the separating step are carried out "in line".

* * * * *

SEQUENCE LISTING

```
<160> NUMBER OF SEQ ID NOS: 1

<210> SEQ ID NO 1
<211> LENGTH: 159
<212> TYPE: PRT
<213> ORGANISM: Homo sapiens

<400> SEQUENCE: 1

Met Arg Leu Glu Glu Leu Lys Arg Leu Gln Asn Pro Leu Glu Gln Val
1               5                   10                  15

Asn Asp Gly Lys Tyr Ser Phe Glu Asn His Gln Leu Ala Met Asp Ala
            20                  25                  30

Glu Asn Asn Ile Glu Lys Tyr Pro Leu Asn Leu Gln Pro Leu Glu Ser
        35                  40                  45

Lys Val Lys Ile Ile Gln Arg Ala Trp Arg Glu Tyr Leu Gln Arg Gln
    50                  55                  60

Glu Pro Leu Gly Lys Arg Ser Pro Ser Pro Pro Ser Val Ser Ser Glu
65                  70                  75                  80

Lys Leu Ser Ser Ser Val Ser Met Asn Thr Phe Ser Asp Ser Ser Thr
                85                  90                  95

Pro Phe Ala Arg Ala Pro Val Gly Lys Ile His Pro Tyr Ile Ser Trp
            100                 105                 110

Arg Leu Gln Ser Pro Gly Asp Lys Leu Pro Gly Gly Arg Lys Val Ile
        115                 120                 125

Leu Leu Tyr Leu Asp Gln Leu Ala Arg Pro Thr Gly Phe Ile His Thr
    130                 135                 140

Leu Lys Glu Pro Gln Ile Glu Arg Leu Gly Phe Leu Thr Leu Gln
145                 150                 155
```